United States Patent
Wilson (12) 
(10) Patent No.: US 6,498,042 B1
(45) Date of Patent: Dec. 24, 2002

(54) PTFE MATRIX IN A SAMPLE INLET LINER AND METHOD OF USE

(75) Inventor: William H. Wilson, Newark, DE (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/525,864

(22) Filed: Mar. 15, 2000

Related U.S. Application Data (63) Continuation of application No. 09/015,607, filed on Jan. 29, 1998, now Pat. No. 6,093,371.

(51) Int. Cl.[7] .............................................. G01N 30/16
(52) U.S. Cl. ..................... 436/174; 73/23.39; 73/23.41; 95/89; 96/105; 422/89; 422/99; 436/161; 436/180; 436/181
(58) Field of Search ..................... 422/89, 99; 73/23.41, 73/23.42, 864.81, 23.39; 95/89; 96/105; 436/161, 174, 180, 181

(56) References Cited

U.S. PATENT DOCUMENTS

| | | | |
|---|---|---|---|
| 4,035,168 A | | 7/1977 | Jennings |
| 4,234,315 A | * | 11/1980 | Scott |
| 5,347,844 A | | 9/1994 | Grob et al. |

OTHER PUBLICATIONS

Fielder et al., Analytical Chemistry, vol. 45, No. 13 (Nov. 1973), p. 2304.*
Matsuoka et al., "Application of Teflon Particle Column to an Odor–Sensing System", Sensors and Actuators, B, 13–14 (1993) pp. 358–361.
Mol etal., "Large Volume Injection in Capillary GC Using PTV Injectors: Comparison of Inertness of Packing Materials", J. High Resol. Chromatography, vol. 18, Feb. 1995, pp. 124–128.

* cited by examiner

*Primary Examiner*—Jan Ludlow (57) ABSTRACT

A sample inlet liner includes a novel matrix that serves to retain an injected sample. The preferred inert matrix is polytetrafluoroethylene (PTFE) that serves to retain an injected sample and is provided in lieu of a conventional packing material. The contemplated inert matrix may be selected from a range of configurations of PTFE so as to provide a supporting material capable of retaining an ample quantity of injected sample in the sample inlet liner. The contemplated matrix nonetheless provides a tortuous path for the retained quantity of injected sample so as to facilitate known injection techniques such as split/splitless injection and large volume injections.

15 Claims, 7 Drawing Sheets

PTFE MATRIX IN A SAMPLE INLET LINER AND METHOD OF USE

CROSS REFERENCE TO RELATED APPLICATIONS

This application is a Continuation application based on and claiming priority to U.S. patent application Ser. No. 09/015,607, filed on Jan. 29, 1998, now U.S. Pat. No. 6,093,371.

FIELD OF THE INVENTION

The present invention relates to chromatographic analysis systems and, more particularly, to a sample introduction system and related apparatus for analyzing a sample comprised of one or more components to determine the identity and concentration of each component in the sample. More specifically, this invention is related to a sample inlet liner and related apparatus fabricated from inert material(s) to reduce sample adsorption or decomposition.

BACKGROUND OF THE INVENTION

Chromatography is a known method of analyzing a sample comprised of one or more components to qualitatively determine the identity of the sample components as well as quantitatively determine the concentration of the components.

A typical chromatographic apparatus includes: a sample introduction system having an injection port, into which the sample is injected and mixed with an inert fluid at high temperature; a column through which the various dissolved components of the sample will travel at a rate related to the characteristics of the specific components; and a detector for measuring the presence of each component.

Analytical chromatography involves a series of steps: sample collection, sample preparation, sample introduction into the chromatographic system, chromatographic separation into individual components, detection of those components, and data acquisition and reduction. For each step, the analyst must make appropriate choices among accepted procedures and available instrumentation. Improper selection or use of the sample introduction system can dramatically limit the performance of the system and, therefore, the ultimate performance of the analytical method. Because of the great variety of columns and the diversity of samples that can be analyzed with modern chromatography, several sample introduction systems and related injection modes are known; no single system can best satisfy all analytical requirements.

However, a common function of the sample introduction system is to provide accurate, reproducible, and predictable introduction of sample into the column. Usually the sample introduction system includes a device known as a sample inlet, whereby a quantity of sample in a liquid form is injected using a syringe. There are other sample introduction devices that introduce samples into the chromatographic column when syringe injection is inappropriate (for example, with solid samples): a gas or liquid sampling valve, head space autosampler, thermal desorber, purge and trap sampler, or pyrolyzer.

Sample inlets are usually divided into two major categories: packed column inlets and capillary column inlets. The types of capillary column inlets are known to include: capillary direct, split/splitless, programmed temperature vaporizing (PTV), and cool on-column direct. Nearly all capillary inlets are vaporizing, including on-column direct injection, except for cool on-column injection, which deposits condensed sample directly into the column.

A useful technique for introducing a liquid sample into a chromatographic system is by injection into a hot inlet wherein it is quickly vaporized (flash vaporization). The benefits of flash vaporization includes the transfer of the liquid sample to a gas and a quick transfer of a sample into the column. However, typical problems associated with vaporizing inlets include band broadening, needle discrimination, inlet discrimination, and sample decomposition. Sample decomposition is indicated by lost or misshapen peaks, or by the generation of unwanted peaks. Decomposition is exacerbated by high inlet temperatures, long residence time of the sample in the inlet, and chemical activity of the sample with the inlet. These problems are exacerbated by the use of high inlet temperatures and low boiling point solvents.

Accordingly, an inlet liner may be positioned in the inlet to reduce chemical activity between the sample and the inlet. The selection and construction of the inlet liner has a direct effect on the success of an analysis, and each type of inlet is designed to function best with a certain type of liner. For example, splitless inlets may require straight liners with no packing, whereas liners constructed for other techniques, such as programmed temperature vaporization, require baffled or packed liners to retain a liquid sample during cold sample introduction.

The inlet liner and any packing material therein is expected to be non-reactive with respect to the compounds and solvents that may be present in an injected sample. One conventional approach is to chemically deactivate the liner and its contents. Deactivation reagents such as hexamethyldisilazane (HMDS), dimethyldichlorosilane (DMDS), and polymethylhydrosiloxane (PMHS) are typical examples. In another approach, a stationary phase coating may be applied to a particulate (such as Dexsil-300 on Chromosorb 750) to achieve a deactivated surface. Such a procedure may only be effective for a limited series of analytical runs, after which the liner must be cleaned and again be deactivated. Thus, conventional approaches can be unsatisfactory, as will now be described.

Note that any sample decomposition will undesirably degrade the minimum detectable level (MDL) of the chromatograph. Low detection levels are important in environmental, pharmaceutical, food analysis, and other gas chromatography applications. Improvements in sample handling, sample injection techniques, and detectors have all contributed to the ability to measure compounds at decreasing levels.

Sample decomposition is especially undesirable in large volume injection (LVI), which is an important technique for lowering the minimum detection level. In LVI, a large volume of sample is injected. The bulk of the solvent is evaporated before the transfer of the sample to the analytical column is initiated. Large volume injection is especially useful in trace analysis to improve analyte detectability, for analysis of, e.g., pesticides and pollutants. Very often it can replace an off-line evaporation step carried out to concentrate a diluted sample extract.

New inlets and injection techniques supporting large volume injection (LVI) have been developed in recent years. Accordingly, there are two primary techniques used to eliminate solvent: 1) via a programmable temperature vaporizer (PTV) inlet; and 2) via a cool on-column injection with solvent vapor exit (COC-SVE). Programmed temperature vaporizing injectors (PTV) have been shown to be well-suited for large volume sample introduction in capillary gas chromatography (cf., e.g., Wilson et al., "Large Volume Injection for Gas Chromatography Using a PTV Inlet", Application Note 228-374, Hewlett-Packard Company, March 1997). LVI with PTV is ideal for trace analysis of later-eluting solutes (i.e., solvents having boiling points approximately 100° C. higher than the solvent) and for dirty samples.

Note that the typical injection volume for capillary column analysis is 0.5 to 2 $\mu$l. The Hewlett-Packard HP 5890 and HP 6890 series gas chromatographs allow approximately two times the normal injection volume (up to 5 $\mu$l, depending on the solvent) using "pulsed" splitless injection, injecting still larger volumes with standard techniques can lead to contamination of the system, irreproducible results, and loss of sample. In contrast, the typical injection volumes employed in a large volume, solvent elimination PTV inlet are 25 to 100 $\mu$l; even up to 1 ml have been demonstrated. Multiple injections can be used with the PTV inlet when even larger volumes are required.

Hence, for large volume injections, the PTV inlet is often used in a "solvent vent" or "solvent elimination" mode. Sample is introduced into the inlet with the inlet temperature near the boiling point of the solvent and with a relatively high split ratio. The solvent (and low-boiling solutes) is vented while the higher boiling solutes (more than about 100° C. above the solvent boiling point) remain and are concentrated in the inlet. After a predetermined period, the split vent is closed and the inlet temperature is increased to transfer the solutes and any residual solvent to a column for separation. Because the sample is evaporated from the inlet, nonvolatile sample components and degradation products remain behind in the inlet, minimizing column contamination. Thus, the PTV inlet is chosen more often than cool-on-column or split/splitless inlet for receiving dirty samples. Hence the PTV inlet is advantageous for cold split or splitless applications and avoids most of the problems associated with hot inlets such as sample discrimination, liner overload, and sample decomposition.

Two injection techniques for large volume injection (LVI) are known: controlled speed injections and multiple injections. In controlled speed injections, the sample injection rate is matched to the solvent vaporization rate such that the liner is not overfilled with liquid during the sample injection. Hence the inlet liner capacity is not a limiting factor, but the injection rate must be slowed to an appropriate speed.

In multiple injections, an aliquot of sample that does not exceed the liquid capacity of the liner is introduced to the inlet. The solvent is allowed to evaporate before the next aliquot is injected. This approach has several advantages over controlled speed injection. However, at least one of the disadvantages of multiple injections is the single shot liner capacity: for a typical liner (e.g., a multibaffle liner) the liner capacity is approximately 5 $\mu$l. Thus, to make a 100 $\mu$l injection, 20 replicate injections must be made. A larger liner can reduce the number of replicate injections and minimizes adverse effects such as vial cap septum coring and contamination, but such liner construction suffers from other disadvantages, such as its cost, size, etc.

Liner capacity may be increased by packing the liner bore with a support material in order to provide a physical support for retention of the liquid sample in the liner bore after injection. Several materials are known; the typical choice is quartz or glass wool, which provides good permeability as well as a large surface area for holding solvent. A typical liner packed with glass wool has an injection capacity of at least 35 $\mu$l. Another approach is to pack the liner with glass beads or particulates used for packing chromatographic columns, such as Tenax TA or Dexsil-300 coated on Chromosorb 750 (commercially available from Chrompack, Bergen op Zoom, The Netherlands). The small particles (35–200 mesh size) are porous and offer large surface area for holding solvent.

Mol et al., in "Large Volume Injection in Capillary GC Using PTV Injectors", J. High Resol. Chromatogr., 18, 124–128, (February 1995), describe use of a variety of packing materials, including silanized glass wool, which is often used and which affords reliable results for thermostable compounds such as polycyclic aromatic hydrocarbons and polychlorobiphenyls. However, the authors conclude that the use of silanized glass wool as packing material in a large volume sample introduction with a PTV injector causes decomposition of thermolabile or polar compounds because the glass wool exhibits an undesirable interaction between the sample and active sites on the surface of the wool fibers. As a result there is degradation or adsorption of the analytes when present in the liner.

The authors also found certain alternatives to glass wool-packed liners that were more inert than glass wool and were better suited as packing material in large volume sample introduction for analytes covering a broad volatility and polarity range. Their preferred alternative was a PTV inlet packed with PTFE wool or a packing material composed of the above-described Dexsil-coated Chromosorb material. With regard to the packing material composed of Dexsil-coated Chromosorb material, the authors describe only their use of hexane and ethyl acetate as a sample solvent. Neither of these solvents would be expected to dissolve Dexsil; however, other solvents are capable of such dissolution. Accordingly, the Dexsil-coated packing material has limited use as it would not be suitable for use with a solvent capable of dissolving such a coating.

The other preferred packing material. i.e., PTFE wool, is described by the authors as being prepared from a PTFE rod, and is cited as having a maximum inlet temperature of 275° C. The authors therefore appear to teach the use of PTFE wool only for use in inlets subject to lower temperatures; in fact, the authors recite the basis of their choice of PTFE as being its water resistance.

Accordingly, for analyses of pesticides and pollutants, wherein polar and thermally-labile compounds are so prevalent, the foregoing approaches are less than satisfactory because of temperature limitations or due to sample decomposition due to interaction of those compounds with the inlet liner and the packing material. For example, the above-described use of PTFE wool is attractive, except that a maximum temperature limit of 275° C. which precludes the use of PTFE wool at higher temperatures that would be useful in certain applications. Moreover, the large surface area offered by glass or PTFE wool enhances solvent capacity but nonetheless also offers a multitude of sites for analyte adsorption or decomposition. Organophosphate pesticides such as Guthion, Acephate, and Methamidophos are prime example of difficult compounds that may be subject to adsorption or decomposition. Lastly, it is difficult to pack a typical liner with PTFE wool in a reproducible way such that the maximum sample volumes and solvent vent times do not vary.

For the foregoing reasons, there remains a need for an improved packing material for use in all types of an inlet liners including, but not limited to, split/splitless inlets and PTV inlets. Ideally, the packing should be highly inert and thermostable. The packed liner should retain the high-boiling analytes only as necessary in order to minimize the thermal stress applied to these compounds upon splitless transfer to the column. Furthermore, the packing should be compatible with common organic solvents and the inertness should not be affected by their use. The packed liner should retain a large volume of liquid sample in order to allow rapid introduction of large sample volumes without overloading the liner capacity. The packing material should be applicable to a typical liner in a reproducible way such that the maximum sample volumes and solvent vent times do not vary.

Also for the foregoing reasons, there remains a need for an improved liner for use in all types of an inlet liners including, but not limited to, split/splitless inlets and PTV inlets. Ideally, the liner should be highly inert and thermostable. The liner should be compatible with common organic solvents and its inertness should not be affected by their use. The liner should be amenable to packing so as to retain a large volume of liquid sample in order to allow rapid introduction of large sample volumes without overloading the liner capacity. The liner should also be amenable to receiving packing material in a reproducible way such that the maximum sample volumes and solvent vent times do not vary.

SUMMARY OF THE INVENTION

I have determined that a conventional liner is not amenable to deactivation by conventional methods to an extent sufficient for the analysis of certain samples, such as those that traditionally react with the sample inlet liner, such as analytes containing organophosphates (e.g., pesticides) and organochlorines.

I have further determined that the packing material used in conventional liners, such as deactivated glass wool, glass beads, or sintered glass particles, is not amenable to deactivation by conventional methods to an extent sufficient for the analysis of certain samples, such as those containing organophosphates or pesticides.

According to the present invention, a novel sample inlet liner may be constructed according to the present invention to offer improved performance when subjected to certain samples, and generally overcomes the foregoing problems in the prior art.

In a preferred embodiment of the invention, a sample inlet liner may be provided to include a novel matrix that serves to retain an injected sample and is provided in lieu of a conventional packing material.

In another preferred embodiment, a novel sample inlet liner may be constructed to include an internal barrier surface of PTFE and further includes an inert matrix of PTFE that serves to retain an injected sample and is provided in lieu of a conventional packing material.

In another feature of the invention, the contemplated inert matrix may be selected from a range of configurations of PTFE so as to provide a supporting material capable of retaining an ample quantity of injected sample in the sample inlet liner. The contemplated matrix nonetheless provides a diffusion path for the retained quantity of injected sample so as to facilitate known injection techniques such as split/splitless injection and large volume injections.

In another feature of the invention the contemplated matrix avoids the filamentary, or "wool"-like construction of the prior art and therefore is believed to be useful at a higher operating temperature range, i.e., in excess of 275 degrees Centigrade. With respect to the prior art packing materials, the contemplated matrix is expected to be less subject to thermal degradation, adsorption, contamination, and the deleterious effects of mechanical working.

In another feature the invention, the contemplated sample inlet liner may be manufactured easily and inexpensively.

In another feature the invention, the contemplated matrix may be positioned in the bore of the sample inlet liner in an easy, consistent, and reproducible manner, thus allowing more predictable performance in large volume injections.

In another feature of the invention, the contemplated matrix is thermally and mechanically stable to an extent sufficient for use in a traditional hot split/splitless inlet.

In another feature of the invention, the contemplated sample inlet liner is easily manufactured from commercially available tubing stock, or may be applied to the interior of the sample inlet liner according to known techniques such as vapor deposition. Preferred embodiments of the sample inlet liner may be manufactured, cleaned, or replaced in a fashion that is easier and less costly than with conventional liners.

Preferred embodiments of the invention are contemplated for use in a wide range of sample inlets, such as split, splitless, split/splitless, and programmable temperature vaporization (PTV) inlets. Additional applications of the preferred embodiments include other sample introduction systems and thermal desorption systems.

BRIEF DESCRIPTION OF THE DRAWINGS

In the drawings and in the following detailed description of the invention, like elements are identified with like reference numerals. Note that, for the purpose of clarity in illustration, FIGS. 1–5 include schematic illustrations rep-

DETAILED DESCRIPTION OF THE PREFERRED EMBODIMENTS

The method of the present invention may be employed to improve the detection of a variety of sample compounds present in a fluid in an analytical chromatographic system. Such fluid is intended to include gases, liquids, multiple component gases and liquids, and mixtures thereof capable of regulated flow. Gases are the preferred fluids according to the practice of the present invention, and therefore the following description of the invention will be directed to a gas chromatographic analytical system. However, it should be understood that the teachings herein are applicable to chromatographic analysis of gases, liquids, and other compressible fluids.

In analytical chemistry, liquid chromatography (LC) and gas chromatography (GC) techniques have become important tools in the identification of chemical sample components. The basic mechanism underlying chromatographic analysis is the separation of a sample chemical mixture into individual components by transporting the mixture in a carrier fluid through a specially prepared separation column having a retentive media therein. The carrier fluid is referred to as the mobile phase and the retentive media is referred to as the stationary phase. The principle difference between liquid and gas chromatography is that the mobile phase is either a liquid or a gas, respectively. The analytical choice between liquid and gas chromatography techniques is largely dependent on the molecular weight of the components to be analyzed. Liquid chromatography devices are capable of analyzing much heavier compounds than gas chromatography devices. However, in some instances gas chromatography detection techniques are more sensitive and therefore may be preferred.

"Gas chromatographic analysis" refers generally to an analysis wherein an inert carrier gas is passed through a temperature-controlled column which contains a stationary phase in the form of porous sorptive media, or through a hollow capillary coated with the stationary phase. A sample of the subject mixture is injected into the carrier gas stream and passed through the column. As the subject mixture passes through the column, it separates into its various components. A detector, positioned at the outlet end of the column, detects each of the separated components contained in the carrier fluid as they exit the column.

"Liquid chromatographic analysis" refers generally to an analysis similar to gas chromatographic analysis wherein the principal difference is that the mobile phase is a liquid rather than a gas.

"Detector" refers to a physiochemical data output means, and in particular to means for providing sample peak data representative of information useful as a chromatogram, and includes a wide variety of useful chromatographic detectors, such as the flame ionization detector (FID), photoionization detector (PID), nitrogen phosphorus detector (NPD), flame photometric detector (FPD), thermal conductivity detector (TCD), atomic emission detector (AED), electrolytic conductivity detector (ELCD), and electron capture detector (ECD). Mass spectral detectors and infrared spectral detectors are also known.

"Matrix" refers to an arrangement of PTFE material in a discrete or continuous form that offers a controlled array of interstices, channels, and the like that is sufficient to provide a tortuous path for a sample injected into the array, whereby the matrix is suitable for temporary retention of the injected sample. Exemplary arrangements of PTFE in discrete form include: a) PTFE formed in granular, particulate, beaded, chopped, chipped, or rod-like pieces which may be compacted to form an aggregation; b) stacked or otherwise organized arrays of porous PTFE members, preferably in the form of porous plugs, discs, meshed fibers, sheets, or pads, that may be combined to form an aggregation; and c) a porous PTFE member formed as an open-cell foam, sponge, plug, bolus, or cylinder. Exemplary configurations of PTFE in continuous forms include: a) PTFE formed as a tape or strand that is compacted to form an open-cell mass, plug, bolus, or cylinder; b) PTFE formed as a strand that is arranged in a bobbin or similar form, then removed as a unit, to assume a wrapped, bundled, interlocking, or woven configuration. An arrangement of PTFE to be avoided is a random filamentary mass of PTFE, described in the prior art and hereinabove as "PTFE wool", which is believed to offer insufficient thermal and mechanical stability for certain applications.

"PTFE" refers to polytetrafluoroethylene, which is a known fluoropolymer resin commonly available under the tradename "TEFLON" from sources such as DuPont Fluoroproducts, Wilmington, Del.

Figure 1A:
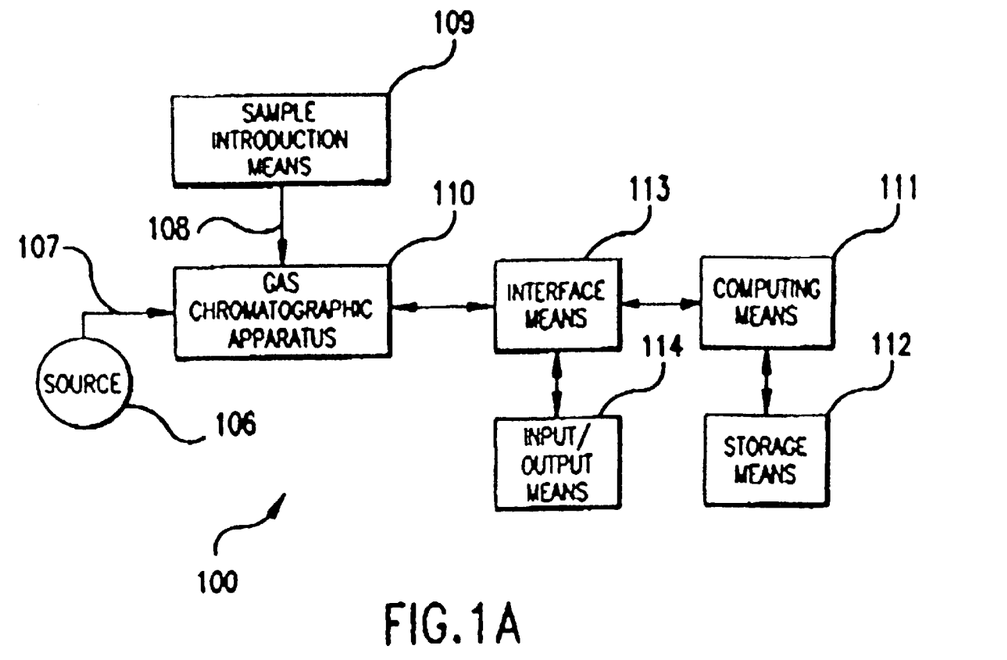
FIG. 1A is a block diagram of an analytical apparatus suitable for the practice of the present invention.
Figure 1B:
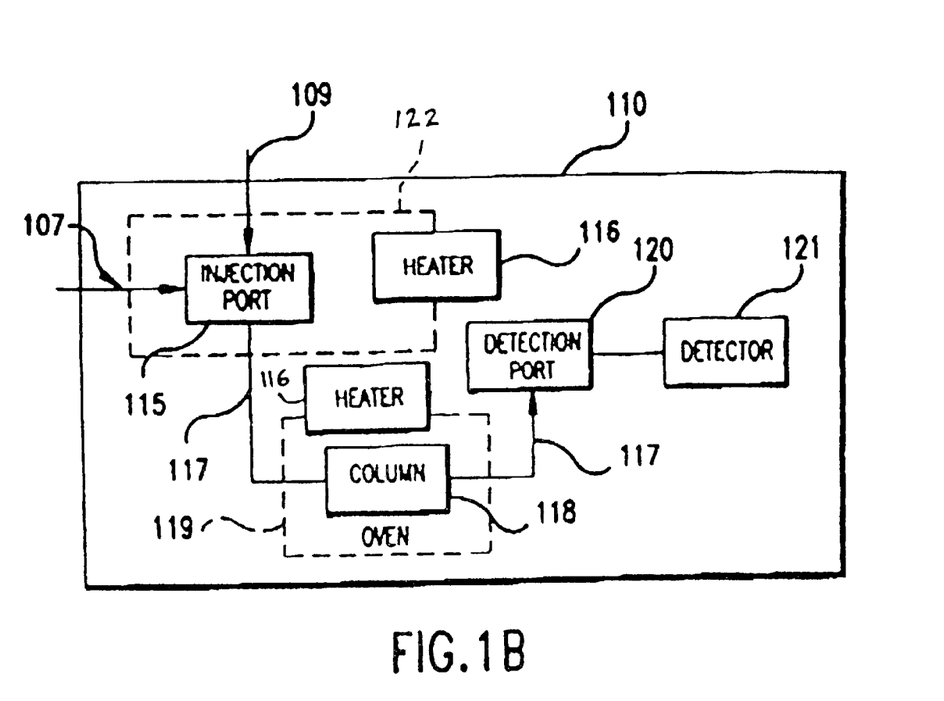
FIG. 1B is a block diagram of a chromatographic apparatus which may be utilized with the apparatus of FIG. 1.

A preferred embodiment of an analytical instrument system 100 is illustrated in FIGS. 1A, 1B. The system 100 includes sample introduction means 109, a chromatographic apparatus 110, computing means 111, storage means 112, interface means 113, and input/output means 114. In order to perform a chromatographic separation of a sample, introduced on line 108, a quantity of the sample is injected into a fluid stream, preferably in the form of a pressurized carrier gas, by means of a novel sample inlet 122 having an injector port 115 that is supplied with a carrier gas stream. The carrier gas is supplied on source line 107 to the inlet 122 from a source 106. The carrier gas may comprise one or more component gases—such as, for example, hydrogen, nitrogen, or helium—depending upon the particular chromatographic separation to be performed.

The inlet 122 provides a portion of the sample/carrier gas mixture to a separation column 118. The column 118 is positioned within a temperature-controlled thermal chamber, or oven 119. The inlet 122 and the oven 119 preferably are temperature controlled by way of respective heaters 116. In order to ensure that the temperature within the oven 119 is at a desired level, the temperatures in the inlet 122 and oven 119 is provided to interface 113 and the computing means 111. The heaters 116 maintain controlled temperatures in the inlet 122 and oven 119 in response to control signals generated by the computing means 111. The carrier gas/sample combination passing through the column 118 on line 117 is thereby exposed to a temperature profile. Typically, the temperatures are controlled according to a selected program so that the sample will separate into its components.

As the carrier gas (containing the sample) exits the column 118, the presence of one or more sample constituent components is detected by a detector 121. The detector 121 can be any of the GC detectors known in the art, so long as it is capable of determining at least one physicochemical property of the sample components which exit the column 118. The detector output signal is then received by the computing means 111 and optionally stored in the storage means 112. Preferably, the detector output signal is provided in the form of data representative of a series of sample peaks in at least one sample peak series. The sample peaks may be identified and presented in one or more sample peak series.

Each sample peak series is analyzed with aid of a peak identification method based on data representative of one or more selected standard peak groups. Preferably, data representative of the standard peak group(s) has been predetermined or inputted at the input/output means 114 and stored in the storage means 112.

The computing means 111 may include computing devices amenable to the practice of this invention, e.g., one or more computing devices such computers, microprocessors, micro controllers, switches, logic gates, or any equivalent logic device capable of performing the computations described hereinbelow. Computing means 111 preferably is coupled with interface means 113 and information input/output means 114; the latter preferably includes a keyboard, keypad, or computer mouse, or remote processor (not shown) for inputting operating condition parameters, system data, and the like. Information input/output means 114 may include display means such as an alphanumeric or video display, a printer, or similar means. The preferred processor 111 may further include storage means 112 in the form of volatile and non-volatile memory devices in which input and output information, operating condition parameters, system information, and programs can be stored and retrieved. Operating commands, device and fluid type information, detector response attributes, column temperature programs, and other information necessary to perform a chromatographic analysis may be entered into the processor 111 by way of the input/output means 114 or retrieved from storage means 112. Messages prompting the user to enter certain information, such as a desired operating parameter, can be generated by the processor 111 and displayed on the display. The interface means 113 may further comprise network and bus system (input/output or I/O) controllers, isolation devices, clocks, and other related electronic components for performing control, processing, and communication tasks other than those described herein.

Figure 2A:
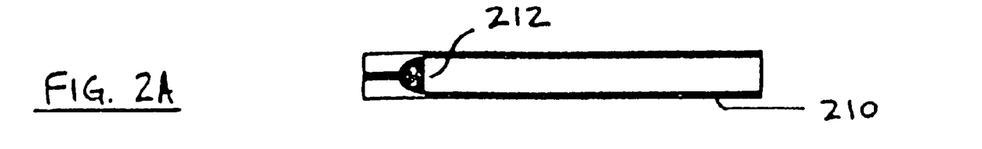
FIGS. 2A through to 2H are side sectional views of preferred embodiments of a sample inlet liner constructed according to the present invention for use in the sample introduction means of FIGS. 1A–1B.
Figure 2B:
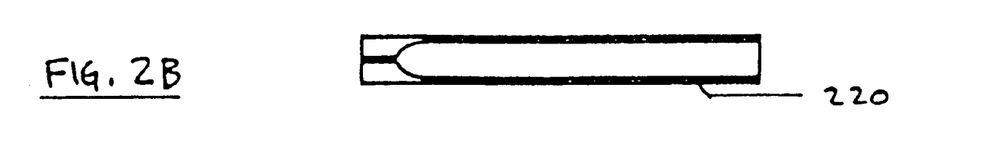
Figure 2C:
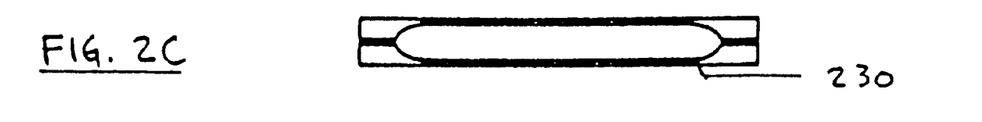
Figure 2D:
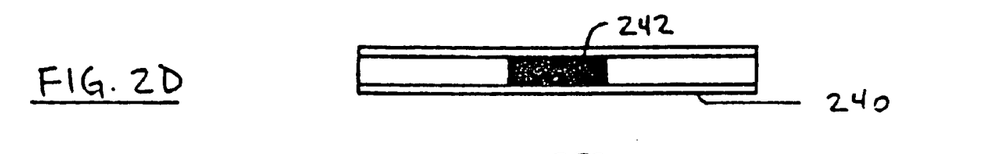
Figure 2E:
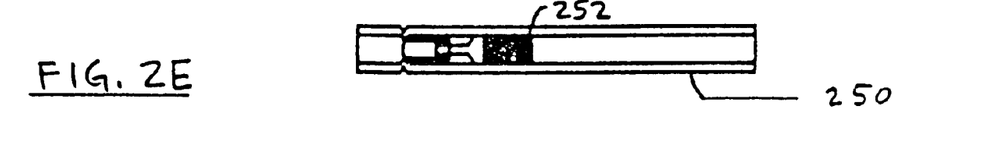
Figure 2F:
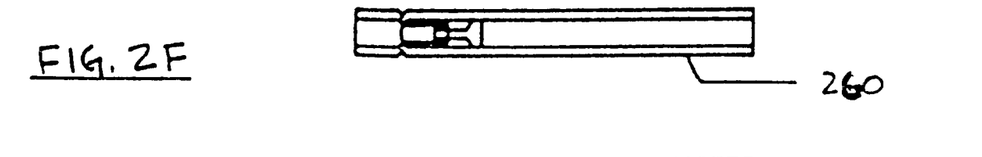
Figure 2G:
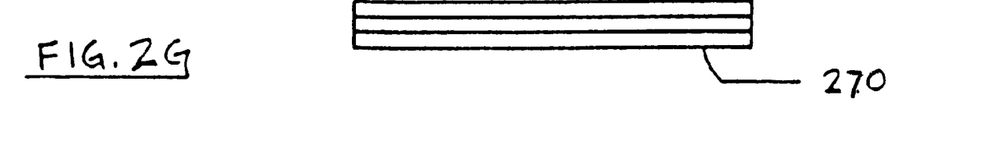
Figure 2H:
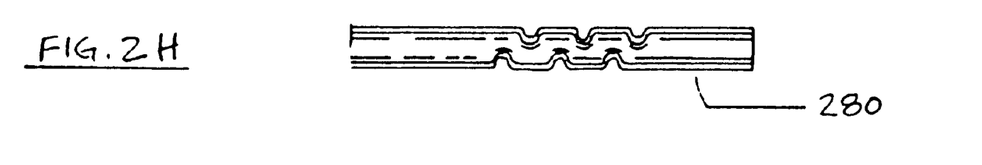

FIGS. 2A through to 2G are side sectional views of respective preferred embodiments of a sample inlet liner constructed according to the present invention for use in the sample introduction means of FIGS. 1A–1B. Each illustrated sample inlet liner incorporates a central bore having an inner barrier surface formed of PTFE. Each embodiment is also optionally amenable to an addition of a PTFE matrix so as to allow temporary retention of a sample in the interior bore of the sample inlet liner. FIG. 2A illustrates a single-taper liner 210 having, for example, a matrix 212; FIG. 2B illustrates a single-taper liner 220; FIG. 2C illustrates a double-taper liner 230; FIG. 2D illustrates a split/splitless liner 240 having, for example, a matrix 242; FIG. 2E illustrates a split liner 250 having, for example, a matrix 252; FIG. 2F illustrates a split liner 260; FIG. 2G illustrates a splitless liner 270; and FIG. 2H illustrates a multibaffle liner 280.

Figure 3A:
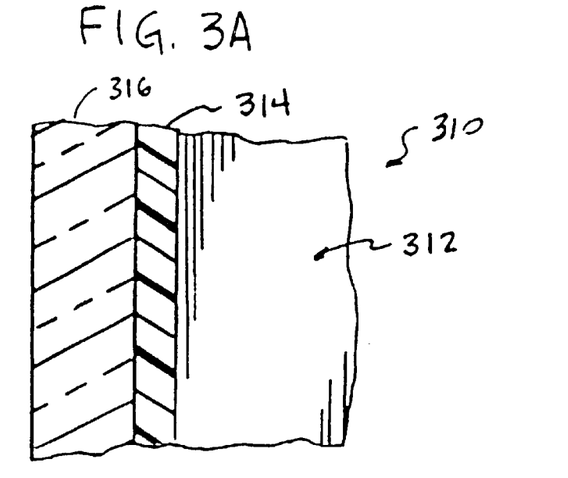
FIG. 3 is a side sectional view of a portion of a selected alternative embodiment with respect to the embodiments of sample inlet liners illustrated in FIGS. 2A–2G, wherein an inner layer of PTFE is provided on a liner jacket.
Figure 3B:
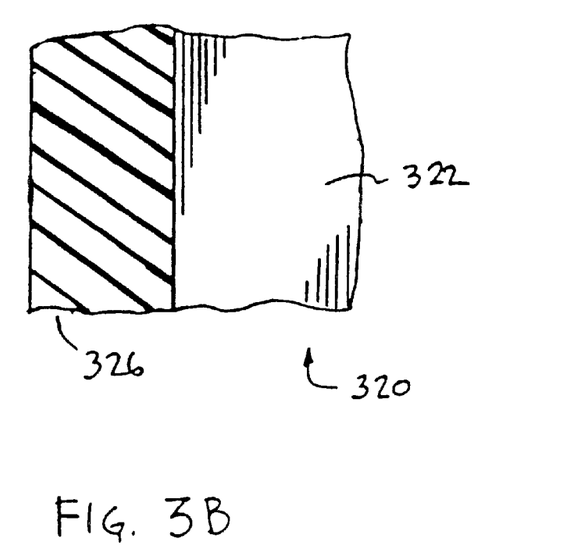

FIGS. 3A and 3B are side sectional views of a portion of a sample inlet liner constructed according to the present invention. The illustrated embodiments are illustrative of representative portions of the sample inlet liners shown in FIGS. 2A–2G.

According to a first feature of the invention, preferred embodiments of the sample inlet liner incorporate an inner bore or channel that is defined by an inner barrier surface composed of a sufficient concentration of PTFE so as to reduce the undesired effects of the presence of a sample that would otherwise react with the inlet, such as the effects described hereinabove as sample decomposition or sample adsorption. Preferred embodiments having the contemplated inner surface may be provided as: a) a PTFE coating on a supporting structure; b) as a component in the composition of an inner surface of a supporting structure, such as in a polymer mixture of one or more polymers with PTFE; c) as a sleeve fitted within a supporting structure; or d) an interior surface on a structure that is itself is composed of PTFE such that the inner surface is composed of PTFE. Other inlet geometries are contemplated as well, presuming that the desired barrier surface is situated in such a way as to reduce decomposition or adsorption of sample when the sample is present in the channel. FIGS. 3A–3B illustrate but two examples.

In FIG. 3A, liner 310 includes a layer 314 of PTFE is situated on a support 316 provided in the form of a hollow tubular jacket so as to define a tubular barrier surface 312. Layer 314 may be provided as a coating of PTFE installed by known methods, such as by vapor deposition of PTFE, or by chemical bonding of PTFE to receptive functional groups in a supporting structure that are capable of bonding to fluorinated oligomers. The layer 314 is contiguous with the support 316, or, in an alternative embodiment, the layer 314 may be provided in the form of a sleeve fitted into the support 316, rather than as a coating. In such an embodiment of the invention, the support 316 may be configured similar to conventional glass or metal liner, whereby the support 316 would provide any necessary mechanical stability and the layer 314 provides the desired barrier surface 312. In this embodiment, the layer 314 can shift coaxially with the support 316 as necessary and would not affect the pressure tightness of the inlet. A flare or lip (not shown) at one end of the layer 314 may be provided such that the sleeve opening will match the outer diameter of the jacket, so as to improve sealing of the liner 310 with attached fittings or other devices, and to limit the sleeve movement within the jacket. In the illustrated embodiment, the support 316 may be composed of known materials such as metal, borosilicate glass, quartz, fused silica, and the like in wall thickness of in the range of approximately 1 millimeter. The layer 314 may of thickness of in the range of approximately 0.1 to 10 microns. Alternatively, the layer 314 may be configured as the aforementioned sleeve in thickness of 100 micrometers to 1 millimeter.

In FIG. 3B, an alternative embodiment includes a tubular member 326 that itself is fabricated to include a sufficient amount of PTFE in its internal surface so as to act as a PTFE barrier layer. Preferably, the member 326 is shaped in the form of a hollow tubular member so as to define a barrier surface 322. In one example, the entire member 326 may be fashioned from PTFE, depending upon the geometry and mechanical characteristics that is needed in the inlet liner. Contemplated geometries include a member 326 having wall thickness in the range of 0.5–3 millimeters.

Note that one or more of the foregoing embodiments may be used to replace a variety of known sample inlet liners. Single taper deactivated splitless liners (Hewlett-Packard part Nos. 5062-3587 and 5181-3316) are but two examples of commonly-used liners that may be replaced by the illustrated embodiment.

It should be understood that the foregoing dimensions are determined by the application of the inlet 310 and thus other configurations and dimensions are contemplated as well.

Figure 4:
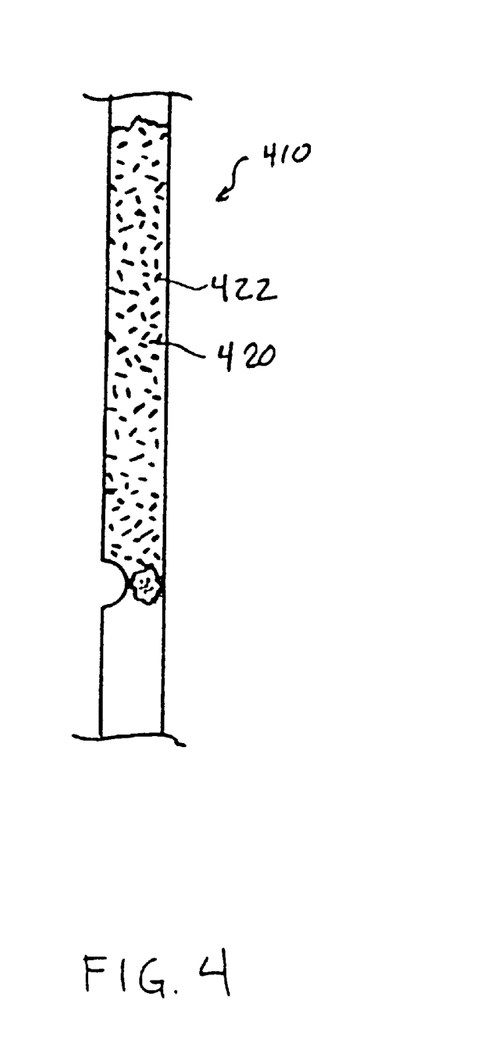
FIG. 4 is a side sectional view of a portion of another embodiment of a sample inlet liner constructed according to the present invention for experimental use.

FIG. 4 is a side sectional view of a portion of a prototype embodiment of a sample inlet liner 410 having a matrix therein constructed according to the present invention. A deactivated glass inlet liner, Hewlett-Packard part number 5183-2036, was modified to include a matrix 420 of PTFE chips 422 packed into the bore of the inlet liner. The chips 422 were cut from PTFE stock commercially available as TEFLON 7A or 850A from DuPont Fluoroproducts, Wilmington, Del. The particles were irregular and ranged in sizes of approximately 0.2 to 0.5 mm in diameter. For the prototype liner, the empty glass liner was first deactivated with a reagent. A particle of PTFE was cut so that it would lodge in the liner indentation, but still provide good permeability. Although spheres, rods, and irregularly-shaped particles were used for the matrix in the prototype development, it is contemplated that other PTFE particle shapes are suitable.

Figure 5:
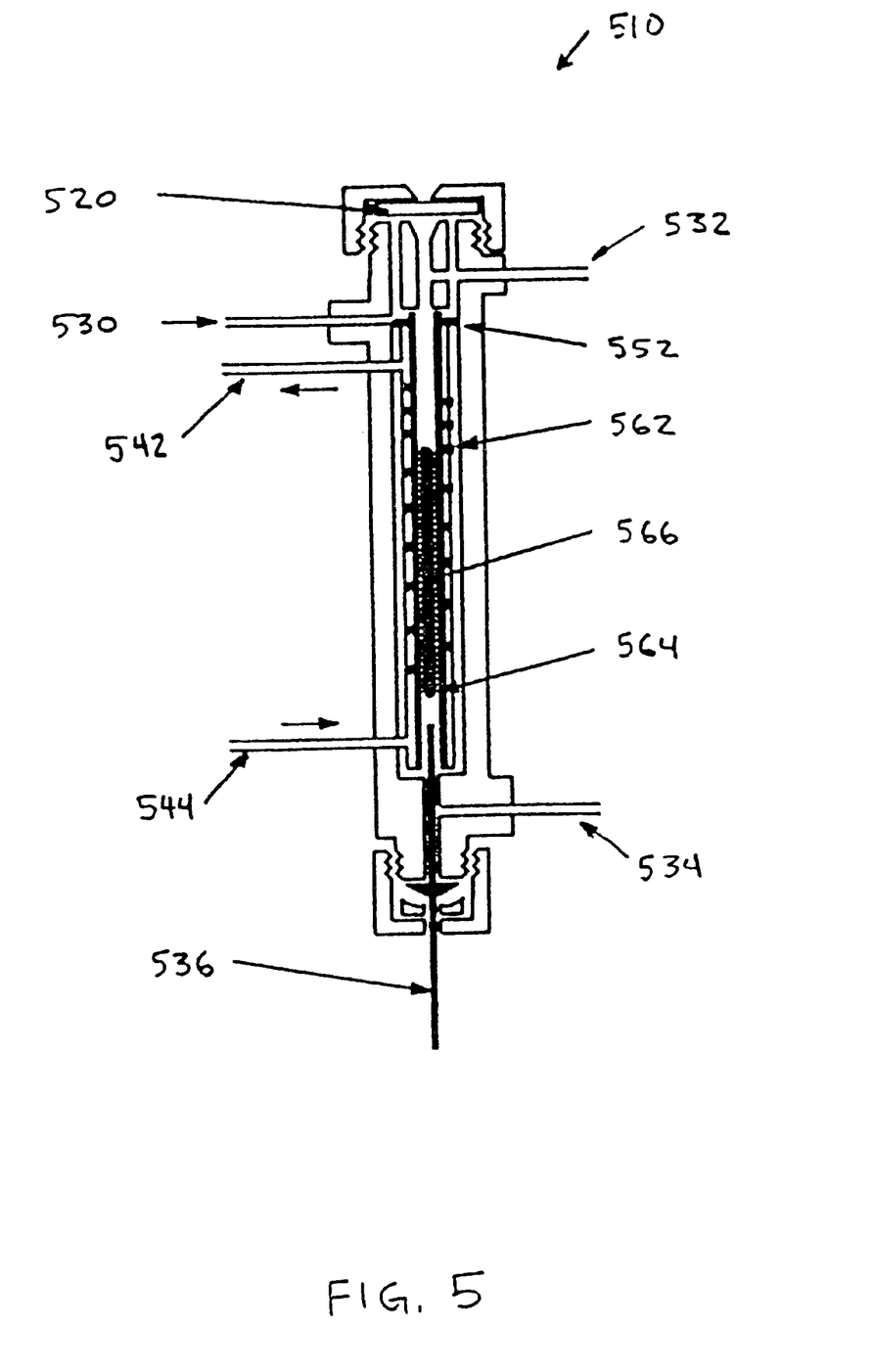
FIG. 5 is a side schematic view of a PTV injector that incorporates a sample inlet liner constructed according to FIG. 2G and which further includes a preferred embodiment of an inert packing material formed of a PTFE matrix according to the present invention.

FIG. 5 is a side schematic view of a PTV injector 510 that incorporates a sample inlet liner similar to the liner 270 of FIG. 2G and which further includes a matrix according to the present invention. One exemplary embodiment of the PTV injector 510 is a modified Hewlett-Packard PTV inlet. The PTV injector 510 can be cooled via cooling lines 542, 544; or heated by use of heaters 562 to 450 degrees C. in up to three ramps, with heating rates as fast as 12 degrees C./sec. The injector 510 includes appropriate ports for pneumatic lines, including a carrier gas line 530, septum purge line 532, split line 534, capillary column 536. The sample inlet liner 564 is preferably constructed according to the present invention to include a matrix 566. The injector 510 is available with a septumless or a septum-containing head 520.

EXPERIMENTAL RESULTS

I. Tests of the prototype liner illustrated in FIG. 4 were performed to examine thermal stability of the prototype liner. Thermal tests to temperatures in excess of 275 degrees centigrade, and up to 350 degrees centigrade, were performed with no apparent decomposition of the PTFE matrix. The criteria for thermostability of the prototype liner were as described by Mol. et al (supra, at p. 125), in that preferred embodiments of the liner were subject to a blank run, and applying a splitless time of 2.5 minutes, wherein no peaks corresponding to an FID response of 0.5 ng of a n-alkane were observed. The results indicated that the preferred embodiments described herein exceed the $T_{max}$ of 275 degrees Centigrade for the inlet having "PTFE wool" described by Mol. et al. Such thermal stability is advantageous when a liner, constructed according to the teachings herein, is to be employed in a variety of applications, such as in a hot split/splitless inlet, as in splitless injections, wherein the analyte may have a residence time in the hot inlet of up to several minutes.

Experimental use of the illustrated prototype indicate that decomposition of Acephate and Methamidophos was reduced as well as the absorption of these compounds. Experimental versions of the illustrated inlet were able to withstand extended inlet temperatures of 300 degrees centigrade and were found to improve the quantitative transfer of organophosphate pesticides.

II. An HP 6890 series gas chromatograph was fitted first with a conventional sample inlet liner, then with the prototype sample inlet liner illustrated in FIG. 4. A series of test analyses of organophosphate compounds was performed to record the performance of each of the two inlet liners. An HP G1916A automatic liquid sampler (ALS) with an HP G1513A controller performed sample injection. An HP 1707A ChemStation (version A.05.01) controlled the instruments and acquired and processed data.

Figure 6:
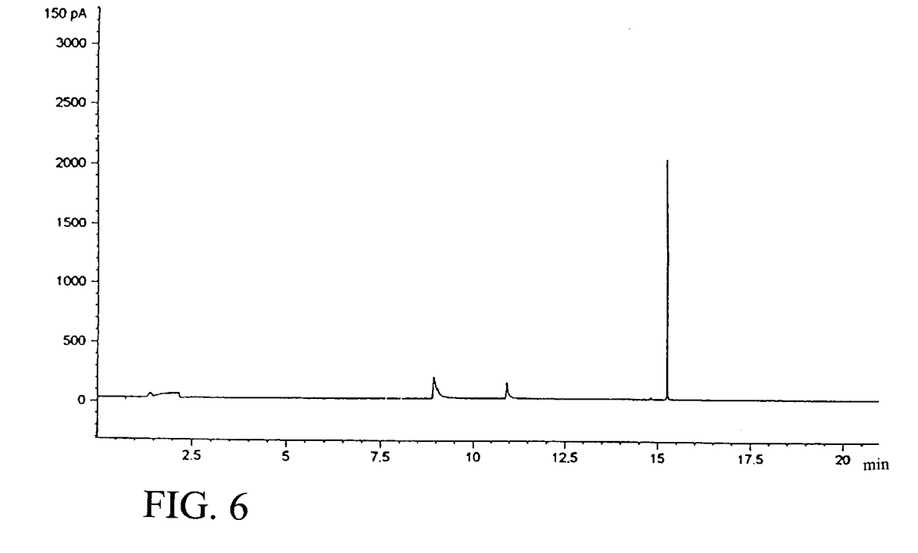
FIG. 6 is a graphical representation of a chromatogram generated with the use of a conventional deactivated multi-baffle sample inlet liner according to the prior art.

FIG. 6 is a diagrammatic representation of a chromatogram generated with the use of a conventional deactivated multibaffle sample inlet liner according to the prior art.

Figure 7:
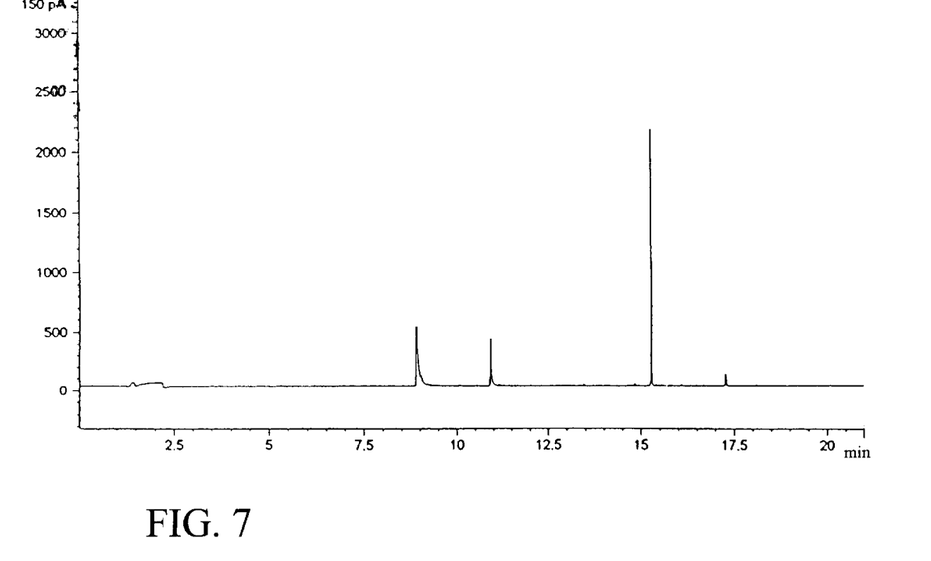
FIG. 7 is a graphical representation of a chromatogram generated with use of a prototype sample inlet liner constructed according to the embodiment shown in FIG. 4.

FIG. 7 is a diagrammatic representation of a chromatogram generated with use of the prototype sample inlet liner of FIG. 4. The sample for these tests consisted of approximately 1 PPM of Acephate, Methamidophos, and Malathion in hexane. The sample (1 ul) was injected under cold splitless conditions. Detection was provided by a flame photometric detector (FPD), with special attention to the phosphorus emission. In order to calibrate the system response, the analytical column was first connected to a cool on-column inlet and the sample was run. The analytical column was then moved to a PTV inlet such as illustrated in FIG. 5 having therein a prototype sample inlet liner as described with reference to FIG. 4, and the sample was re-analyzed.

Figure 8:
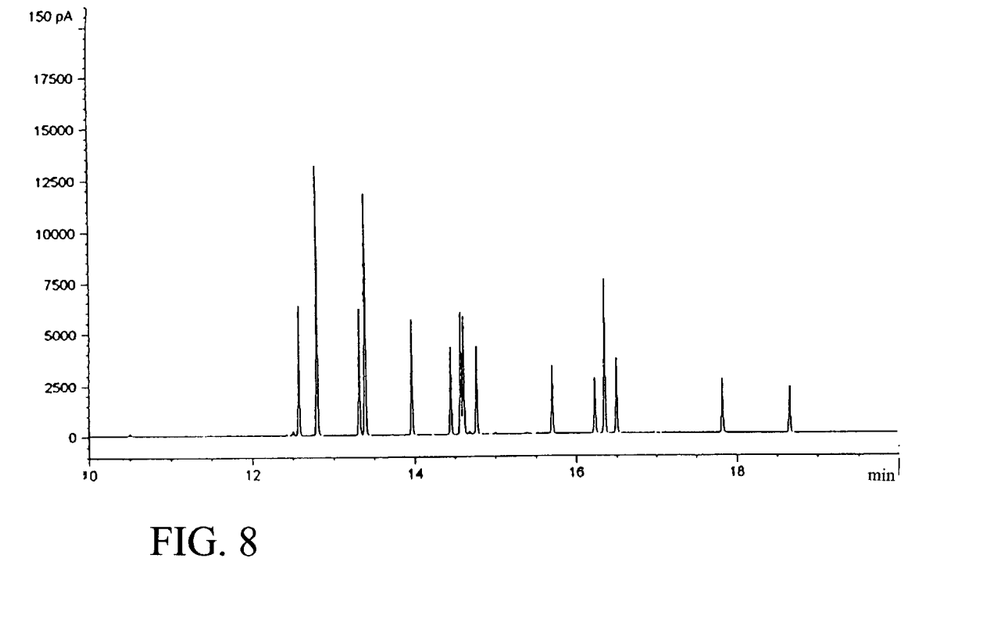
FIGS. 8–10 are graphical representations of further chromatograms generated with the use of the prototype sample inlet liner of FIG. 4 for large volume injections, wherein the sample injections were of combined test mixtures according to U.S. Environmental Agency (EPA) methods 614 and 622, diluted to give equal mass, and applied respectively in 1, 10, and 20 microliter amounts.
Figure 9:
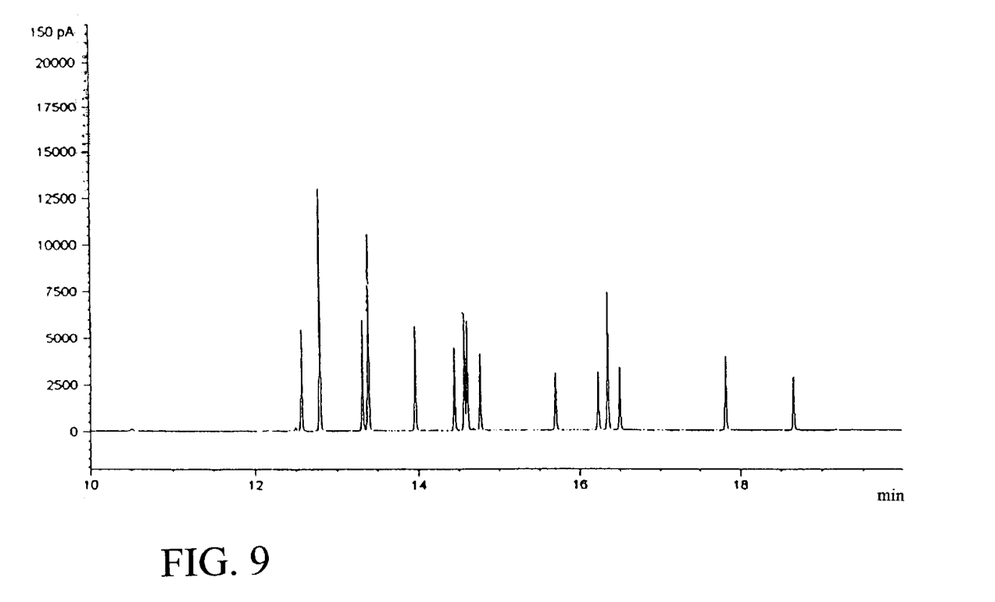
Figure 10:
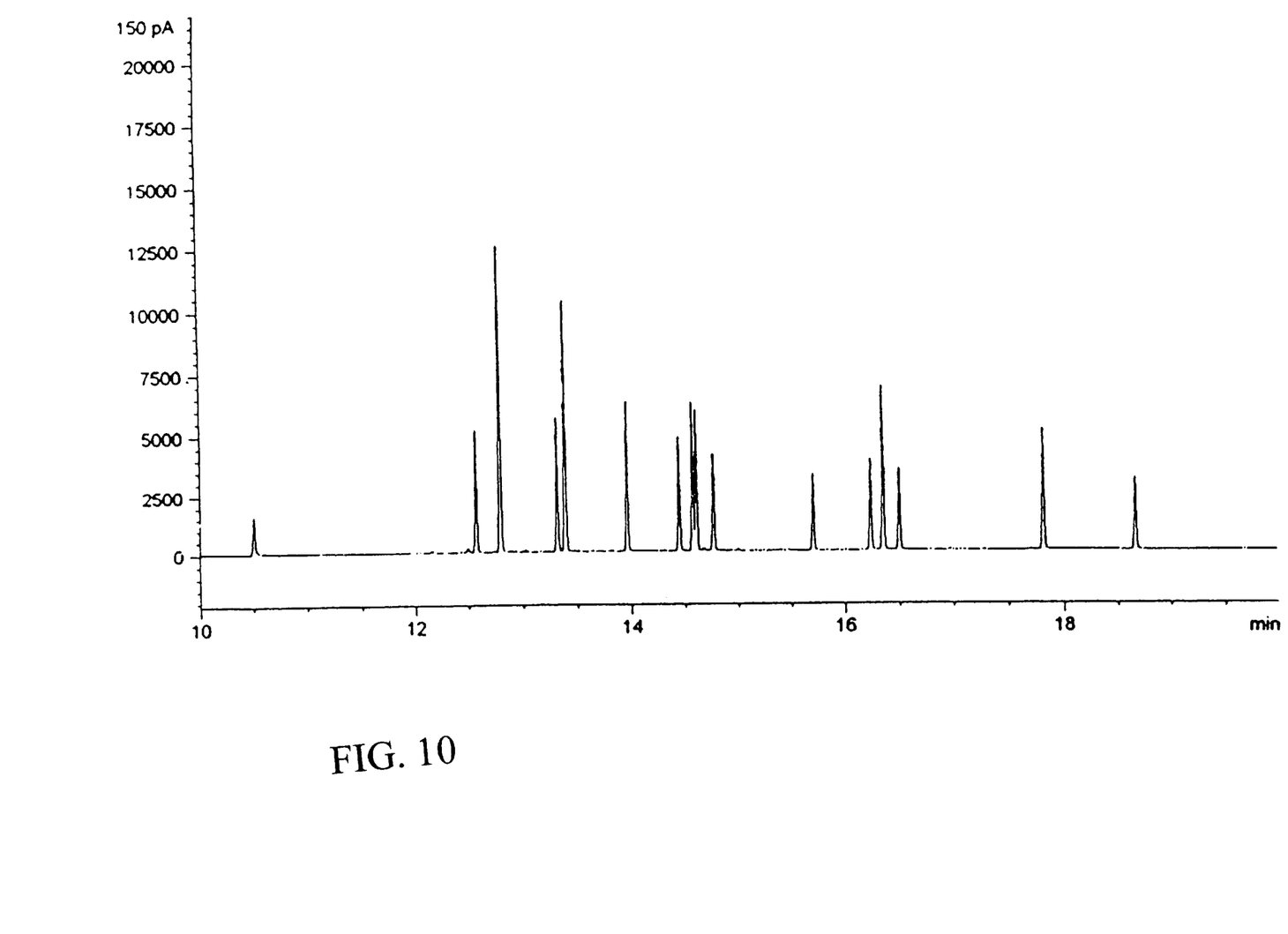

In FIG. 6, the response for the conventional deactivated multibaffle liner indicates Malathion recovery of typically >90%, while the response to Acephate and Methamidophos are closer to only 50%. In contrast, FIG. 7 illustrates a large improvement by the prototype inlet liner in response to Acephate and Methamidophos. Note that the peak tailing for Acephate and Methamidophos is due to the column that was used, not to the prototype inlet. The trace shown in FIG. 7 indicates that both the analyte recovery and peak shape have dramatically improved over the results obtained with the conventional deactivated multibaffle liner To test the liquid capacity of the prototype sample inlet liner, tests directed to injection volume were performed and recoveries were compared to that offered by prior art liners. A 1 ul cold splitless run was made to calibrate the system. A ten-fold dilution was prepared and a 10 ul injection was made in the solvent vent mode. In each case, the sample was diluted to match the injection volume such that the mass of solute introduced was constant. Sample chromatograms are shown in FIGS. 8–10, wherein the sample injections were of 1 PPM of EPA 614 and 622 test mixtures in hexane, applied respectively in 1, 10, and 20 microliter amounts. Sample amounts of up to 25 ul were injected with near quantitative recovery. Hence, a maximum single shot injection volume of approximately 25 $\mu$l can be expected. In comparison, a conventional multi-baffle liner is typically limited to 5 $\mu$l injection volumes. Thus, the single shot injection limit has been increased by a factor of 4 to 5 with improved analyte recovery for organophosphate pesticides.

III. The foregoing experimental results indicate that a sample inlet liner may be constructed as described herein so as to afford: better analyte recovery than a conventional liner when used for detection of difficult compounds, such as organophosphate and other pesticides; and improved inertness to chemically decomposed analytes. Further, the experimental results indicate that a sample inlet liner may be constructed as described herein to include a matrix so as to afford: larger liquid capacity than unpacked, deactivated liners; a higher temperature stability than offered by a liner packed with PTFE wool; and superior resistance to injection solvent, especially compared to inlet liners packed with Dexsil and other stationary phases.

What is claimed is:

1. A sample introduction apparatus for receiving a quantity of injected sample and for providing the injected sample to a chromatographic apparatus, the chromatographic apparatus having a separation column configured for receiving a mixture of a carrier gas and the sample, said sample introduction apparatus comprising:

a support having an inlet and an outlet and defining an internal channel, said inlet being configured to receive the sample, said outlet being configured to provide the sample to the chromatographic apparatus; and a matrix of PTFE located in said internal channel so as to retain the quantity of injected sample and provide a diffusion path for the retained quantity of injected sample, said sample introduction apparatus being configured to be thermally and mechanically stable when heated to temperatures in excess of 275 degrees Centigrade, wherein said support has an injection port in fluid communication with said internal channel, said injection port being configured to receive the carrier gas of the chromatographic apparatus such that said sample introduction apparatus provides the mixture of the carrier gas and the sample to the separation column of the chromatographic apparatus.

2. The sample introduction apparatus of claim 1, wherein the matrix includes an arrangement of PTFE in discrete form selected from the group consisting of: beads, chips, discs, plugs and rod-shaped pieces.

3. The sample introduction apparatus of claim 1, wherein the matrix includes an arrangement of PTFE in organized arrays of porous PTFE members, wherein the members are selected from the group consisting of: meshed fibers and sheets.

4. The sample introduction apparatus of claim 1, wherein the matrix includes an arrangement of PTFE as a porous PTFE member having a configuration selected from the group consisting of: open-cell foam and sponge.

5. The sample introduction apparatus of claim 1, wherein the matrix includes an arrangement of PTFE in continuous form selected from the group consisting of: tape and strand.

6. The sample introduction apparatus of claim 1, wherein the matrix includes an arrangement of PTFE provided in a configuration selected from the group consisting of: wrapped, bundled, interlocking, and woven configurations.

7. A method for providing a quantity of sample to a chromatographic apparatus, the chromatographic apparatus having a separation column configured for receiving a mixture of a carrier gas and the sample, the method comprising the steps of:

providing a chromatographic apparatus;

providing a sample introduction apparatus comprising PTFE;

receiving a quantity of the sample in the sample introduction apparatus;

heating the sample to a temperature in excess of 275 degrees centigrade such that at least a portion of the sample vaporizes; and providing at least a portion of the sample to the chromatographic apparatus.

8. The method of claim 7, wherein the step of providing a sample introduction apparatus comprising PTFE comprises providing a support and a matrix of PTFE, the support having an inlet and an outlet and defining an internal channel, the inlet being configured to receive the sample, the outlet being configured to provide the sample to the chromatographic apparatus, the matrix of PTFE being located in the internal channel and being configured to retain the quantity of sample and provide a diffusion path for the retained quantity of sample.

9. The method of claim 7, wherein the step of providing a sample introduction apparatus comprising PTFE comprises providing a support having an inlet, an outlet and a barrier surface, the inlet being configured to receive the sample, the outlet being configured to provide the sample to the chromatographic apparatus, the barrier surface being at least partially formed of PTFE and defining an internal channel.

10. A chromatographic system comprising:

a sample introduction apparatus for receiving a quantity of injected sample; and a chromatographic apparatus for receiving the injected sample from said sample introduction apparatus, said chromatographic apparatus having a separation column configured for receiving a mixture of a carrier gas and the sample;

said sample introduction apparatus having a support and matrix of PTFE, said support having an inlet, an injection port and an outlet and defining an internal channel, said inlet being configured to receive the sample, said injection port being in fluid communication with said internal channel and being configured to receive the carrier gas of the chromatographic apparatus such that said sample introduction apparatus provides the mixture of the carrier gas and the sample to said separation column of the chromatographic apparatus via said outlet, said matrix of PTFE located in said internal channel so as to retain the quantity of injected sample and provide a diffusion path for the retained quantity of injected sample, said sample introduction apparatus being configured to be thermally and mechanically stable when heated to temperatures in excess of 275 degrees Centigrade.

11. The chromatographic system of claim 10, wherein the matrix includes an arrangement of PTFE in discrete form selected from the group consisting of: beads, chips, discs, plugs and rod-shaped pieces.

12. The chromatographic system of claim 10, wherein the matrix includes an arrangement of PTFE in organized arrays of porous PTFE members, wherein the members are selected from the group consisting of: meshed fibers and sheets.

13. The chromatographic system of claim 10, wherein the matrix includes an arrangement of PTFE as a porous PTFE member having a configuration selected from the group consisting of: open-cell foam and sponge.

14. The chromatographic system of claim 10, wherein the matrix includes an arrangement of PTFE in continuous form selected from the group consisting of: tape and strand.

15. The chromatographic system of claim 10, wherein the matrix includes an arrangement of PTFE provided in a configuration selected from the group consisting of: wrapped, bundled, interlocking, and woven configurations.

* * * * *